(12) United States Patent
D'hondt et al.

(10) Patent No.: US 10,357,329 B2
(45) Date of Patent: Jul. 23, 2019

(54) BONE BED DRILLING TEMPLATE

(71) Applicant: Cochlear Limited, Sydney (AU)

(72) Inventors: Christiane D'hondt, Kruibeke (BE);
Francesca Harris, Leuven (BE);
Rishubh Verma, Antwerp (BE)

(73) Assignee: COCHLEAR LIMITED, Macquarie University (AU)

( * ) Notice: Subject to any disclaimer, the term of this patent is extended or adjusted under 35 U.S.C. 154(b) by 201 days.

(21) Appl. No.: 15/395,953

(22) Filed: Dec. 30, 2016

(65) Prior Publication Data

US 2018/0185114 A1 Jul. 5, 2018

(51) Int. Cl.
| | |
|---|---|
| *A61B 90/00* | (2016.01) |
| *A61B 90/92* | (2016.01) |
| *A61B 17/16* | (2006.01) |
| *A61B 17/17* | (2006.01) |
| *H04R 25/00* | (2006.01) |

(Continued)

(52) U.S. Cl.
CPC .......... *A61B 90/39* (2016.02); *A61B 17/1695* (2013.01); *A61B 17/176* (2013.01); *A61B 17/1742* (2013.01); *A61B 17/1764* (2013.01); *A61B 17/56* (2013.01); *A61B 90/92* (2016.02); *H04R 25/606* (2013.01); *A61B 17/1771* (2016.11); *A61B 2017/564* (2013.01); *A61B 2090/395* (2016.02); *A61B 2090/3916* (2016.02); *A61F 2002/183* (2013.01); *H04R 2460/13* (2013.01)

(58) Field of Classification Search
CPC .. A61B 90/39; A61B 2090/3916; A61B 90/92
See application file for complete search history.

(56) References Cited

U.S. PATENT DOCUMENTS

| | | |
|---|---|---|
| 8,157,862 B2 | 4/2012 | Corbitt, Jr. |
| 2011/0129930 A1 | 6/2011 | Wuister |
| | (Continued) | |

FOREIGN PATENT DOCUMENTS

WO  2012/163397 A1  12/2012

OTHER PUBLICATIONS

International Search Report and Written Opinion in corresponding International Application No. PCT/IB2017/058150, dated Apr. 18, 2018, 13 pages.

(Continued)

*Primary Examiner* — Christian A Sevilla
(74) *Attorney, Agent, or Firm* — Edell, Shapiro & Finnan, LLC

(57) ABSTRACT

A method and device for ensuring better placement of an implant, such as an implant that is affixed via bone bed drilling to a recipient's skull. In particular, the technology comprises an apparatus and method of deploying the same that can lead to an improved goodness of fit of the implant. The apparatus and process of the present disclosure are particularly applicable to affixing auditory prostheses such as cochlear implants. The implant is provided with a template that has the same dimensions as the implant that is to be affixed. This template has a dye-impregnated material on its distal surface that is used during bone bed drilling to identify bony spots that have to be drilled away to get a flat surface and a better alignment of the implant with the bone bed. The template may also be provided in kit form.

30 Claims, 9 Drawing Sheets

(51) Int. Cl.
*A61B 17/56* (2006.01)
*A61F 2/18* (2006.01)

(56) References Cited

U.S. PATENT DOCUMENTS

2012/0165821 A1    6/2012  Carignan et al.
2014/0099604 A1*   4/2014  Kurpis ................... A61C 19/05
                                                   433/223

OTHER PUBLICATIONS

Asher, et al., "Fabrication and use of a surgical template for placing implants to retain an auricular prosthesis", The Journal of Prosthetic Dentistry, vol. 81, No. 2, Feb. 1999, 6 pages.
"Bausch Articulating Papers 'Arti-Check'(R) micro-thin", at http://bausch.fm/Blackbelt/bkdb/bk_templates/bausch/en/products/FMPro.php?-DB=bk_products&-Lay=weblayout&-Format=proderg.html&-SortField=headline_e&-SortOrder=ascend&-Max=1&-Op=bw&artno=40m&-Find (last accessed, Mar. 24, 2017).
Cochlear Limited, "Surgical Instructions for Use—Codacs(TM) DI110 Implant System", p. 12, et seq., Cochlear Limited, Sydney, Australia, (2014).

\* cited by examiner

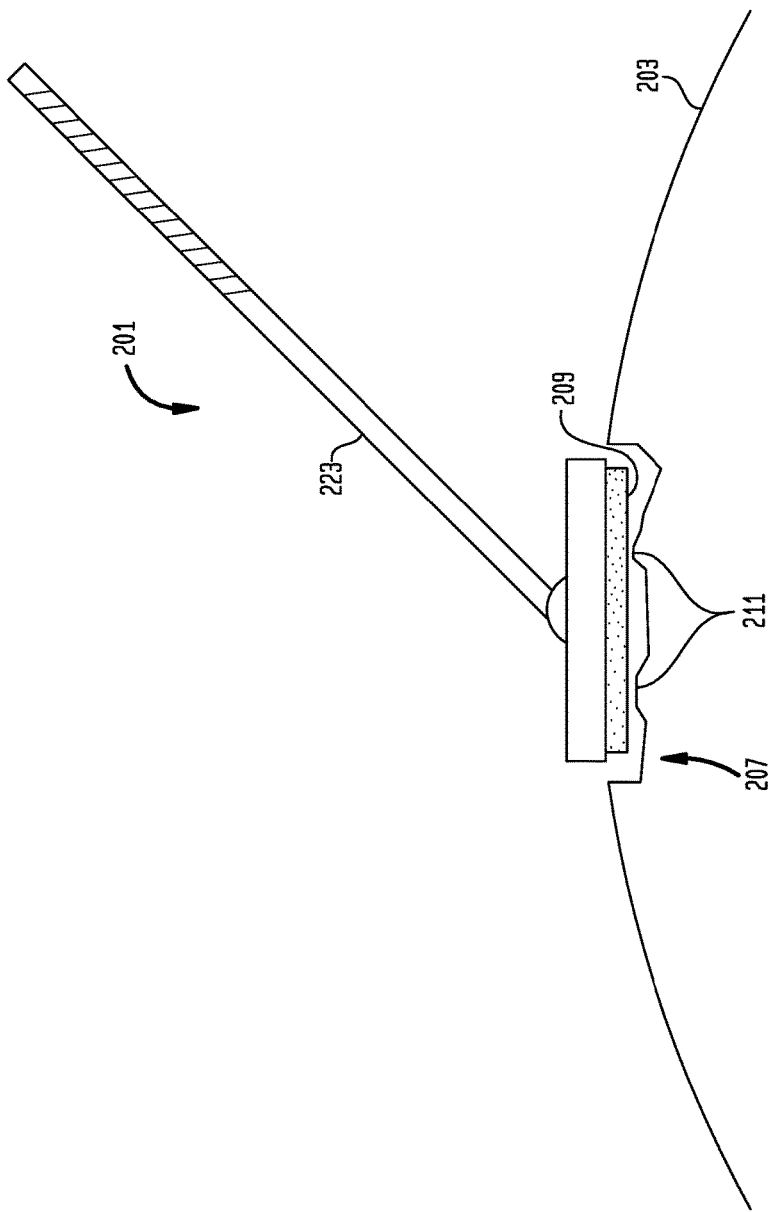

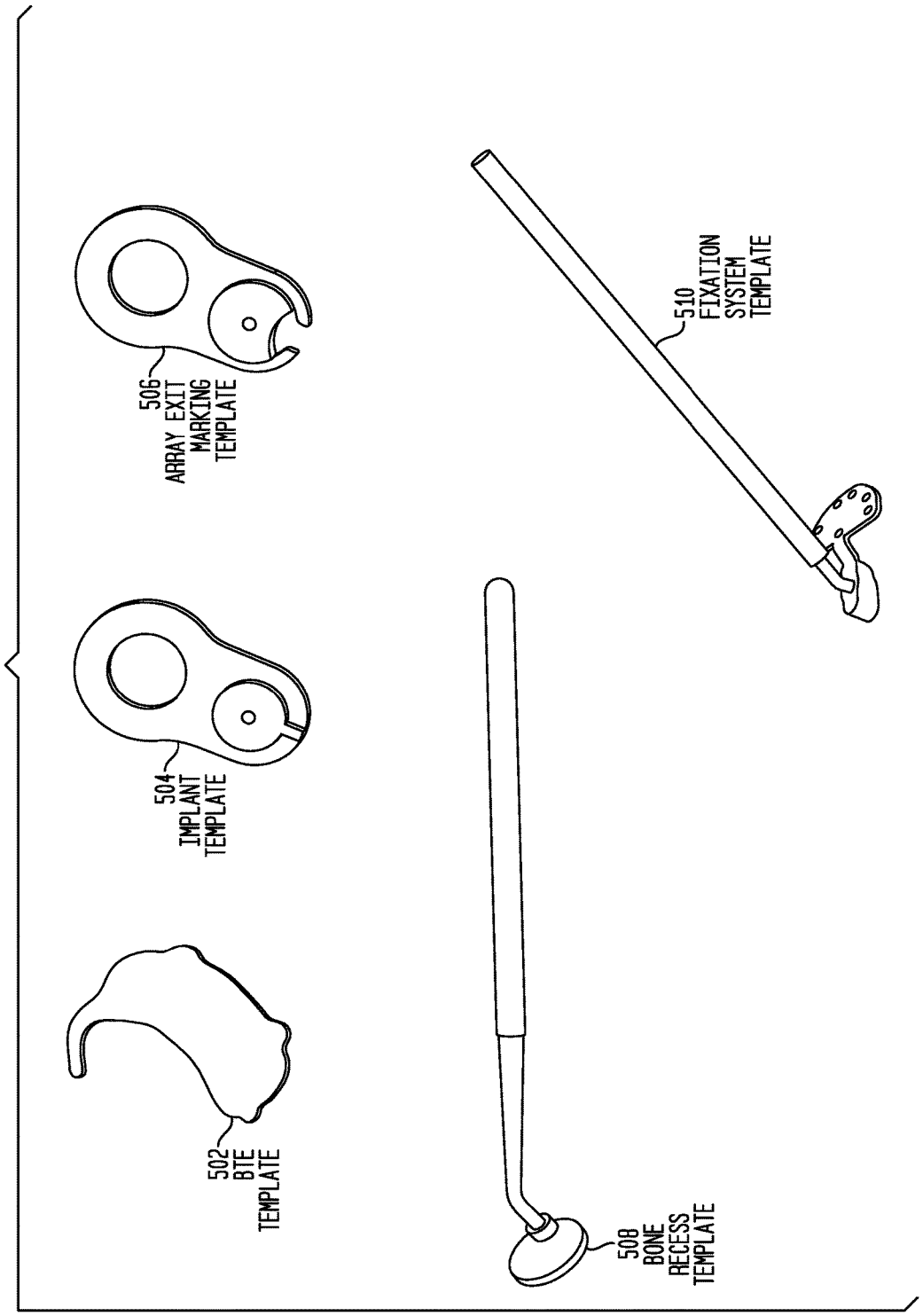

BONE BED DRILLING TEMPLATE

TECHNICAL FIELD

The technology described herein generally relates to placement of medical implants, and more particularly relates to optimizing the closeness of fit of an implant to an area of bone.

BACKGROUND

Bone bed drilling is a time consuming task during implant surgery, in part because of the precision required to ensure a good fit between the implant and the bone surface. The surface of the bone bed to which an implant is attached needs to be smooth and flat, in order to minimize complications such as biofilm formation in interstices between the surface of the bone and the surface of the implant if the bone surface is uneven, or inadvertent relocation of the implant after surgery due to poor contact adhesion if the bone surface is not flat enough.

For an implant that is affixed to a patient's skull these problems are particularly acute since the surface of the skull is curved, yet the surface of an implant is flat. So if an implant is placed directly on to the surface of the skull, it can rock because it is flat relative to the curved section of skull. The surgeon therefore needs to plane away a flat surface of the bone to accommodate the implant in a rigid manner. Additionally, the surface of the recessed portion needs to be as smooth as possible so that the area of contact with the implant is maximized over the recessed region and the implant does not wobble due to unevenness of the surface, and there are no cavities between the bone surface and the adjacent implant surface.

In many types of implant such as auditory prostheses, the portion of the implant that is in direct contact with the bone is a receiver/stimulator unit: if this item does not have good contact with the bone at all points on its surface, it can shift its position after surgery, leading to a degradation or variability in its performance, and a continual need to recalibrate it. Furthermore, cavities, if present underneath the receiver/stimulator, can lead to biofilm formation and higher infection risks for the subject, in the post-surgical phase. Biofilm formation is encouraged when there is a pocket of air between the implant and the bone, in which bacteria can grow. Such bacteria can spread and make an increased area of infection, thereby having a harmful impact on the implant recipient. There can be a similar propensity for biofilm formation in any imperfections that may exist on the edges of the bone bed: it is important that the side walls of the drilled out area are perpendicular to the flat area which was drilled out and this may not be easy to gauge.

Other methods for reducing biofilm include coating the surface of the implant with an anti-bacterial substance, or a material such as a silicone that fills the voids when the implant is affixed, as well as by designing the implant so that it has smooth surfaces. These approaches, however, do not address the goodness of fit of the implant.

Some implants have used a hydroxyapatite cement to affix it but the substance expands on setting and so is less desirable when the implant must fit snugly in the bone bed. Other ways of fixing an implant are by using a titanium bridge, or a suture above the implant, but these methods do not necessarily work well for all types of implant and may not address the issue of biofilm formation.

Many implant kits are provided with a surgical kit containing various implant templates that can be used by surgeons to check the depth, shape, and flatness of the bone bed during drilling and prior to attachment of the implant. Some examples are produced by Cochlear, Limited (e.g., the CI24RE implant template). In many instances, more than one template is required for the same implant because, the same template cannot necessarily be used to define the perimeter of the area before any drilling is done as the template that is used to gauge the proper depth of the recessed area.

FIGS. 1A, 1B, 1C, and 1D show the actuator 101 of an exemplary acoustic implant, its fixation system 111, its position in situ on a patient's skull 103, and a template 121 to assist the surgeon in drilling a recessed area of bone in which to position fixation system 111, and the corresponding receiver/stimulator 141. In this example, fixation system 111 is used to hold actuator 101 in the mastoid (bone behind the recipient's ear), as shown in FIG. 1B, and as further described herein. The receiver/stimulator unit that communicates with actuator 101 is not shown in FIGS. 1A-1C.

However, while implant templates do help a surgeon to create a flat surface by trial and error, they do not make it clear to the surgeon where to flatten the bone, or improve the perpendicularity of the sides of the bone bed, during surgery. Therefore, during bone bed drilling, surgeons often struggle to create a flat surface, and may end up unnecessarily drilling away additional bone at the wrong spots.

In the absence of any other way in the art to address the foregoing problems, there is accordingly a need for a method and device for facilitating reliable placement of a bone implant, in order to improve the efficiency of the surgical process, as well as ensure a greater fidelity of the implant's attachment to the bone surface.

The discussion of the background herein is included to explain the context of the technology. This is not to be taken as an admission that any of the material referred to was published, known, or part of the common general knowledge as at the priority date of any of the claims found appended hereto.

Throughout the description and claims of the application the word "comprise" and variations thereof, such as "comprising" and "comprises", is not intended to exclude other additives, components, integers or steps.

SUMMARY

The instant disclosure is directed to the better placement of a part of an implant, such as an implant that is affixed via bone bed drilling of a recipient's skull in a manner that permits part of the implant, say the actuator, to be properly positioned. In particular, the disclosure comprises an apparatus and method of deploying the same that can lead to an improved goodness of fit of at least part of the implant to the recipient's skull. The apparatus and process of the present disclosure are particularly applicable to affixing auditory prostheses such as cochlear implants.

The apparatus comprises one or more surgical templates that has the same dimensions as the part of the implant that is to be affixed to the recipient. The templates are used during bone bed drilling to identify bony spots that have to be drilled away to get a flat surface and sides that are perpendicular to the bottom, and hence a better alignment of the implant receiver/stimulator with the skull.

The present disclosure provides for surgical templates that can be used to improve the goodness of fit, and minimize biofilm formation, when affixing an implant on a recipient's skull. The templates can be used with many types of implantable audio prosthetic devices, such as cochlear implants, middle ear implants, bone conduction auditory implants, subcutaneous implants, ossio-integrated steady state implants, and direct acoustic cochlear implants.

The templates of the present disclosure are loaded with a dye-impregnated material on a distal surface. When this material makes contact with the recipient's bone, the dye is transferred to the bone at the points where contact is made. Thus a template can be used, in the first instance (before drilling commences) to delineate the area to be drilled. While the recessed area is being drilled out, a template can be inserted one or more times into the drilled area to provide an indication to the surgeon of any unevenness in the surface and/or sides of the drilled region. Such templates are particularly suited for bone bed drilling on a recipient's skull but can in principle be used for an implant affixed to any bone in the human body.

The present disclosure further includes a process for using a surgical template, having a dye-impregnated material on its distal surface, to delineate an area of a recipient's skull to be drilled, and portions of the bone bed to be drilled during surgery.

The present disclosure additionally includes a surgical kit that includes an implant and one or more implant templates having a dye-impregnated material on a distal surface.

BRIEF DESCRIPTION OF THE DRAWINGS

FIG. 2 shows a schematic of a dye template in use on a recipient's skull, checking the goodness of fit.

FIG. 5 shows a kit having a number of templates.

Like reference symbols in the various drawings indicate like elements.

DETAILED DESCRIPTION

The instant technology is directed to methods and devices to improve goodness of fit of a medical implant that is designed to be affixed to a recipient's bone. The technology further includes methods and devices for reducing the possibility of biofilm formation in small unwanted recesses that can arise between the surface of the implant and the surface of the bone when drilling the portion of bone needed to accommodate the implant.

Use of a Template when Affixing a Bone Implant

It is instructive to first describe a method and device of affixing an implant, as used in the art, in conjunction with FIGS. 1A, 1B, 1C, and 1D, which illustrate the nature of the technical problem for an exemplary auditory prosthesis, Codacs™ direct acoustic cochlear stimulator from Cochlear Limited, Sydney, Australia. It would be understood to those of skill in the art that the general principles of affixing such an implant apply to other types of implant, and are not limited to auditory prostheses.

Figure 1A:
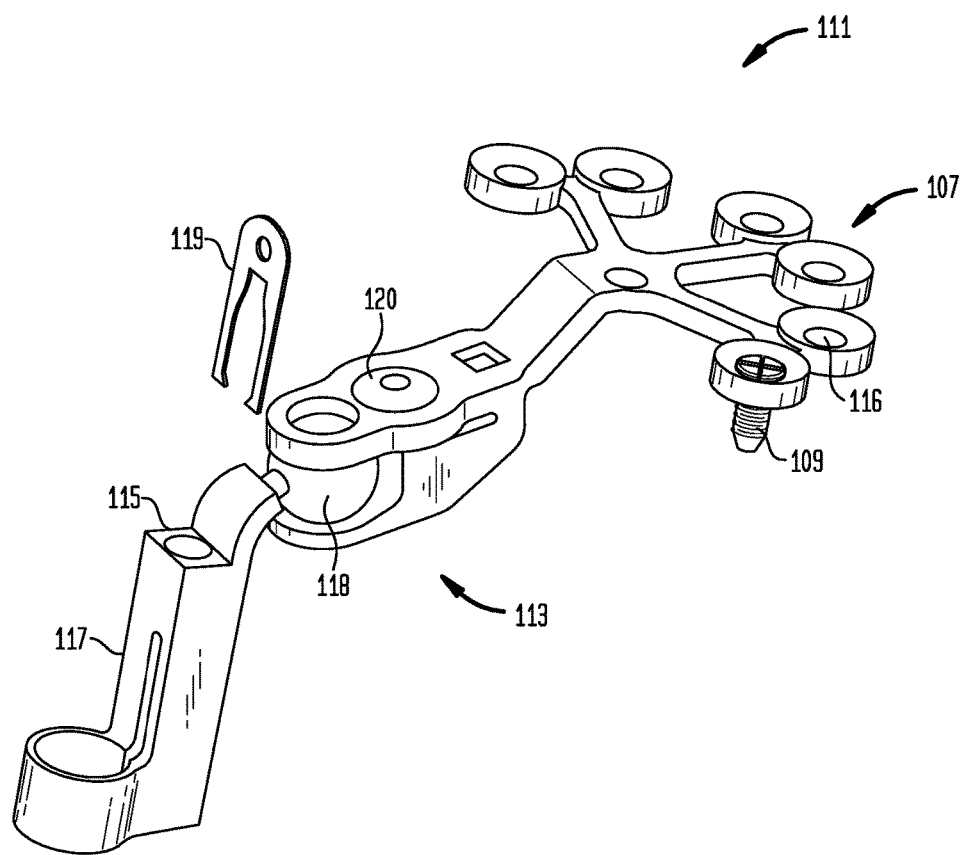
FIGS. 1A-1D show the fixation system of an implant (1A), its location in situ (including the actuator) (1B), a fixation system template (1C), and the entire implant including the actuator and a corresponding receiver/stimulator (1D), as found in the prior art.
Figure 1B:
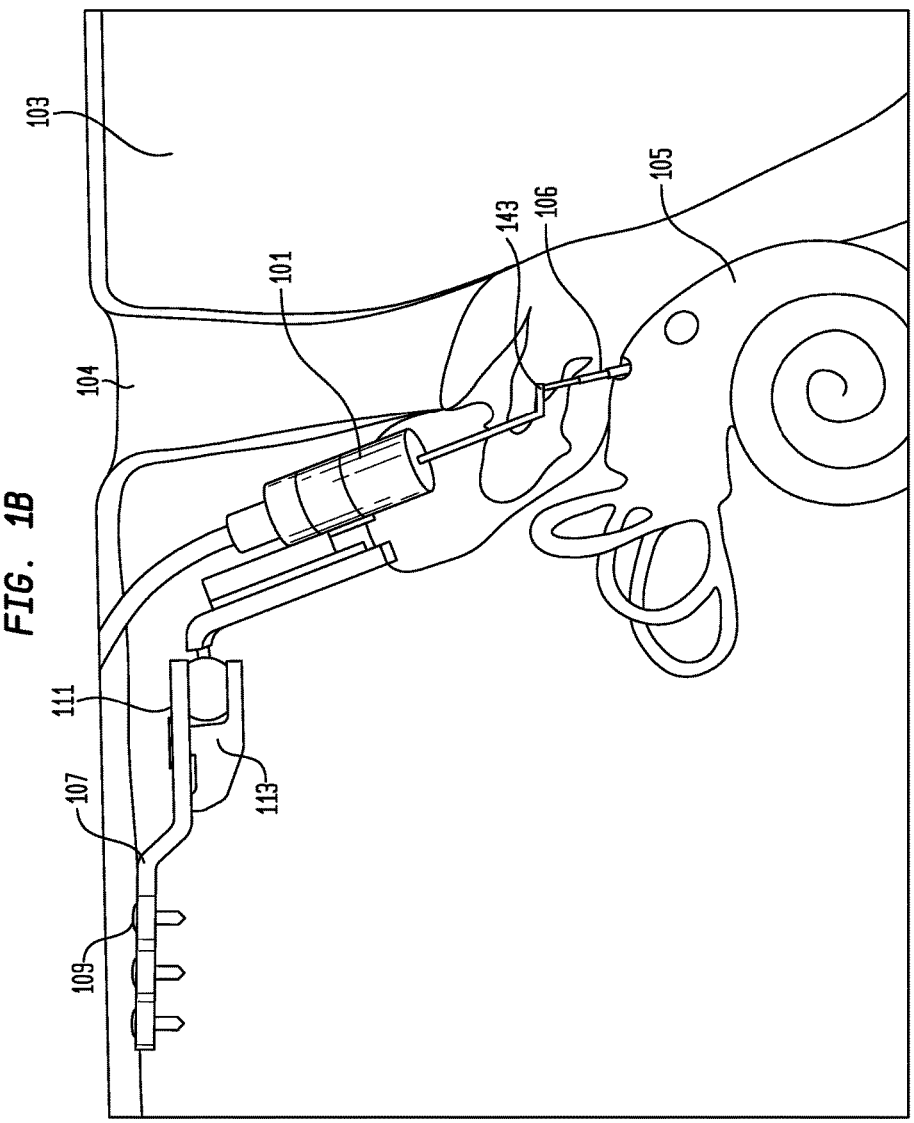
Figure 1C:
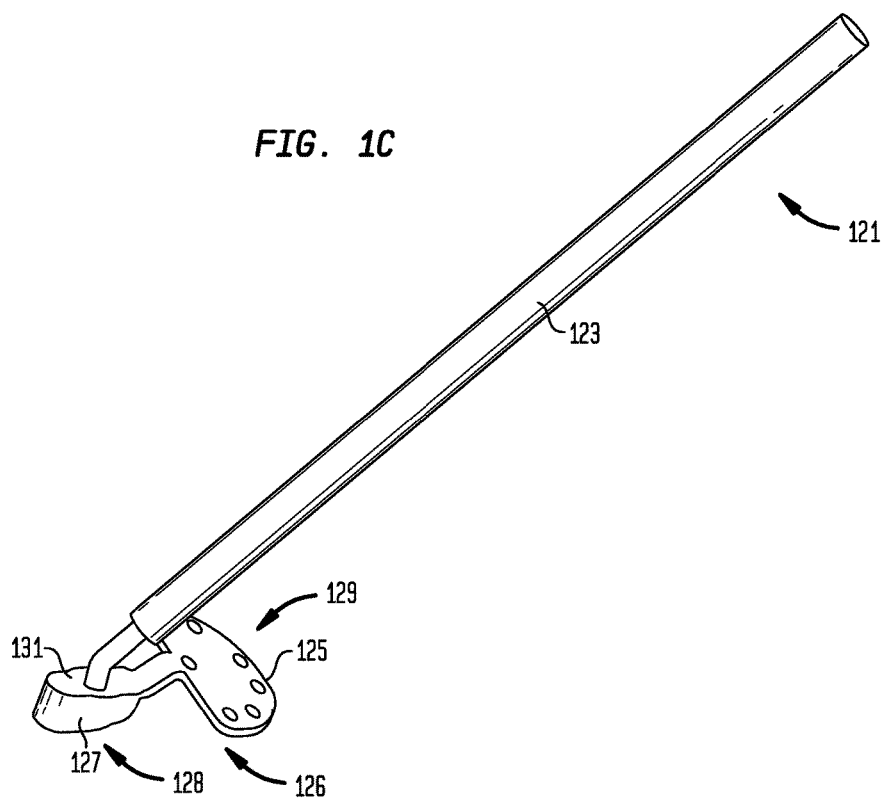
Figure 1D:
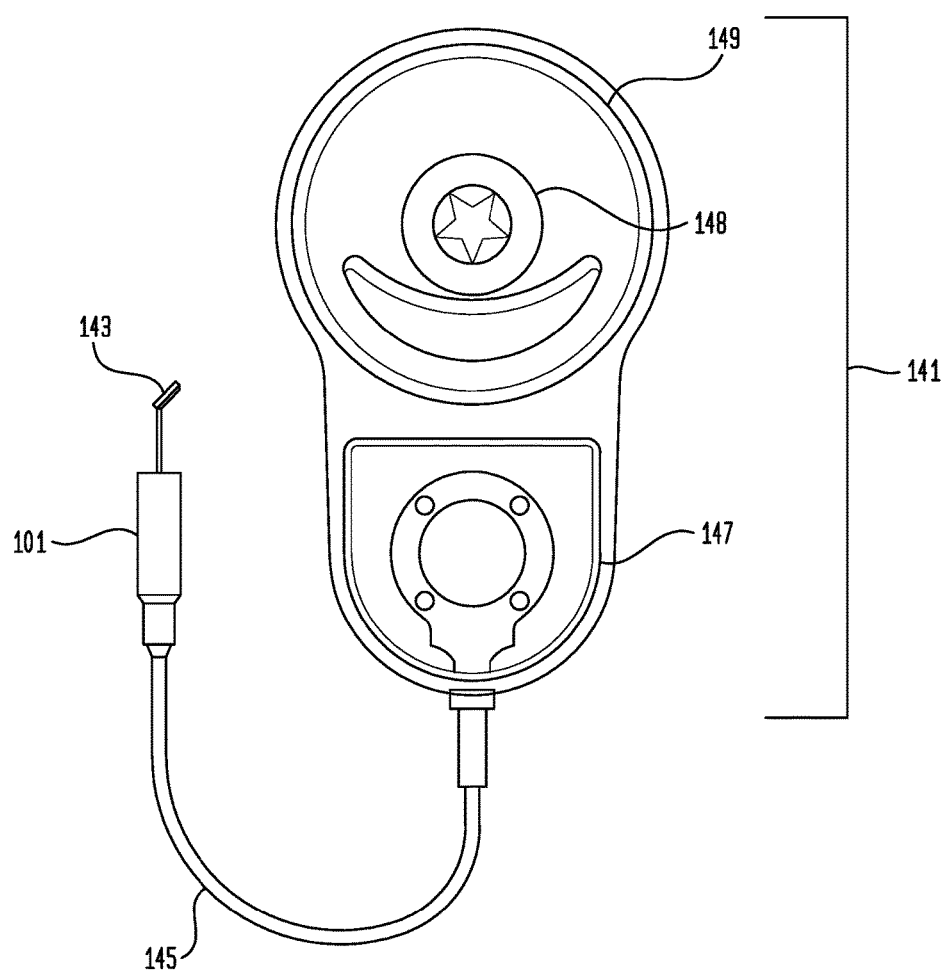

In FIG. 1B, the actuator 101, shown in situ adjacent to a recipient's auditory canal 104, and which stimulates fluid in the recipient's cochlea 105, is held in place by a fixation system 111. The corresponding receiver/stimulator 141 is shown in FIG. 1D, for illustration. Artificial incus 143 is connected to a conventional stapes prosthesis 106, which is inserted into the recipient's cochlea. Lead assembly 145 provides electrical connectivity between the actuator and the receiver/stimulator assembly 141. In this embodiment, the receiver/stimulator comprises various electronic circuitry 147, a magnet 148, and receiver coil 149.

Fixation system 111 is shown in elevation view in FIG. 1A, and in plan view from the side, in FIG. 1B. Fixation system 111 comprises three portions: an attachment portion (bone plate) 107 that lies flat on the recipient's skull and contains a number of holes 116 (seven holes in the embodiment shown), through which screws 109 are inserted, in order to attach the system to the recipient's skull. A pedestal 113, such as comprising a ball joint 118 and ball clamp screw 120, is situated into a drilled out recessed area of the recipient's skull. Clamping mechanism 117 is not affixed to the recipient's skull but holds actuator 101 in its position in the mastoid cavity, wherein it can function effectively. A clamp screw 115 can be used to adjust the position of clamp 117 as well as to secure it in its optimal position. Elastic blade 119 is for locking clamp screw 115.

When affixing fixation system 111 to a recipient's skull, it is necessary to drill out a recessed area of skull that can accommodate ball joint portion 113. The size of the area to be drilled is determined by the model of implant (implants are not designed or tailored for the individual recipient).

While the outer perimeter of the regions to be drilled can usually be defined quite accurately, the depth of the recessed area is more difficult to drill reliably. Accordingly, the surgeon typically uses a gauge, or template, 121 to test the goodness of fit of the portions drilled. Template 121 has a handle 123 held by the surgeon during use, and by which the surgeon positions the template, and portion 127 that replicates the size and shape of ball joint portion 113 of fixation system 111. Portion 125 replicates the size and position of attachment portion 107 and can be used to define where screw holes must be drilled.

At the outset, the surgeon can take a pen and draw around a template—normally a different template—to define the boundaries of the bone bed prior to drilling. (For example, a reliable determination of the perimeter would be difficult with template 121 because it will not contact the skull surface evenly before any recessed area is drilled. Preferably a flat template that just corresponds to the top surface/shape of the implant is used to define the perimeter of the area to be drilled.

Portion 127 of template 121 has a distal surface, 128 that contacts the surface of the bone bed. When properly in situ, only the proximal surface 131 of portion 127 will be visible. Thus, as the surgeon is drilling the recessed regions, the template can be inserted to ascertain whether portion 127 fits snugly into the respective drilled regions. Unevenness can be judged by the surgeon moving the template within the drilled holes, and/or by testing the alignment of the upper (proximal) surface 131 of the template with the adjoining surface of the recipient's skull. The template will typically be inserted in this manner many times during the drilling process until the surgeon is satisfied that the drilled region properly fits the implant fixation system, and the implant can then be attached. The template can be discarded (in the case of a single-use embodiment), or preferably sterilized and re-used on another occasion when the same type of implant is to be installed. The implant itself is already sterilized and may not be re-sterilized by the clinic.

In other embodiments of templates, the tool has a rocking mechanism so that the surgeon can tell how much of the bone to drill away within the recessed area. Such a tool, however, does not reveal how even the section is once it's drilled.

While this method of using a template is known in the art, it is imperfect because it is difficult for the surgeon to gauge accurately which portions of the drilled region may be leading to an unevenness of fit. Thus the surgeon may waste time drilling away portions that are not contributing to unevenness of fit. Additionally, even where the surgeon has drilled away portions that appear to lead to a good fit of the implant, the surgeon has no way of identifying any cavities or crevasses in the drilled region that will create voids between the bone surface and the surface of the implant when affixed. Such voids are undesirable due to the possible build up of biofilm within them, which can lead to infections as well as imperfections of fit.

Use of a Template Having a Dye on a Distal Surface

According to the instant technology, an implant template is provided that has a dye releasing surface on one or more of the distal surfaces. See FIG. 2. When the implant template 201 is pressed into the bone bed 207, the dye is transferred from the dye-releasing distal surface 209 to the areas of protrusion 211 of the bone bed that contact the distal surface of the template. These are protruding regions of the bone that need to be further flattened by drilling and are now readily identifiable to the surgeon as colored regions of contrast relative to their immediate surroundings.

The manner of use of implant template 201 is as follows. The surgeon holds handle 223 of implant template 201 while applying it to the bone surface, or bone bed. There is sufficient dye in the material on the distal surface that the surgeon can put the template in place as many times as necessary during surgery.

The implant template 201 can also be used at the outset to delineate the area of the bone to be drilled out. Prior to starting drilling, the surgeon can place the dye-transfer material on the distal surface of the implant on to the bone surface. The dye colors the bone surface in the shape of the implant and therefore obviates the need to delineate that region in some other way, such as by drawing around the template.

The instant technology can therefore lead to a reduction in time for the surgeon to prepare the bone bed during surgery because, with each application of the template, just those areas that need to be drilled are swiftly identified. This reduces aspects of trial and error from the surgeon's task, and therefore makes for a more attractive implant choice. The resulting better fit of an implant in the bone bed leads to less possibility of biofilm formation and less likelihood of a slippage of the implant after affixation.

Other facets of the technology are described as follows.

The dye transfer material on the distal surface of the implant template can take a number of different forms.

In one embodiment, the dye is absorbed into, or is coated on, some vehicle or carrier, such as an absorbent substance, referred to herein as the dye transfer or dye-impregnated material. The dye transfer material is preferably a non-toxic absorbent material that is capable of releasing the absorbed dye with contact pressure such as when the material is placed in contact with another surface.

The dye transfer material is affixed, as a layer, to the distal surface of the template. In some embodiments the material is initially loaded with a dye substance and, as the template is used and the dye is transferred to the bone bed, the material becomes less concentrated in dye. The material can then be re-loaded with dye, as needed, such as by dipping the material in a dye-containing solution. The dye impregnated material can take the form of a sponge. In another embodiment, the dye-impregnated material is a micro fleece paper with high color storage capacity.

Alternatively, the layer of material can be removed from the template, much as a self-adhesive sticker can be removed, and a new layer of dye transfer material (impregnated with dye) affixed, for subsequent uses of the template.

In another embodiment, the surgeon is provided with a pad, impregnated with the dye, and on which they can contact the distal surface of the template in order to coat it with dye. This can enable use of just the template and the dye, without a dye-impregnated material on the template. For example, when using a titanium reusable template, the dye may simply transfer directly to the titanium surface and thereafter to the recipient's bone bed when pressing the template onto the patient's skull.

Figure 4:
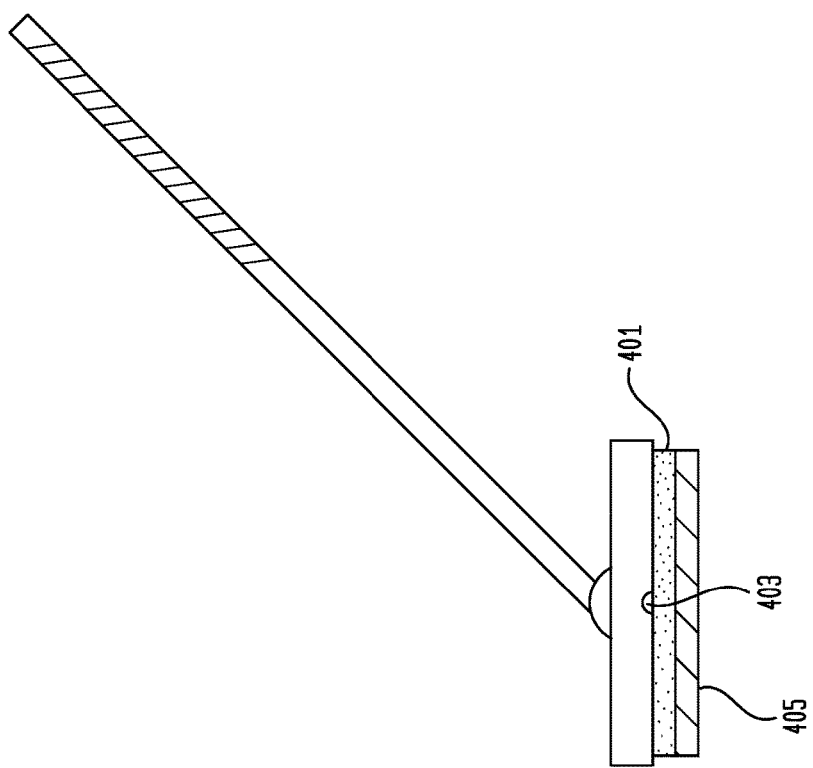
FIG. 4 shows a template having a dye material attached to a mounting layer that clips to the template via a press-button arrangement.

In still another embodiment, the dye material can be clipped onto the template for example, via a press button, see FIG. 4. In this instance, the dye-impregnated material 405 is coated on a plastic carrier 401, which can be moulded with a press button 403 that clips into a matching recessed portion of the distal surface of the template. Such an arrangement can be suitable for a single use.

In preferred embodiments, the templates described herein are made from stainless steel. This makes them easy to sterilize and suitable for multiple re-uses. It can be envisaged that single use templates can be made from other materials, such as plastic.

Exemplary Dyes

Any dye used with the implant template described herein should be biocompatible, which is to say that it should not embody any toxic effects, should not exacerbate or create any adverse reaction in the recipient during use, and should preferably either be capable of being rinsed or rubbed off after surgery or should remain localized at the site of surgery, without leaching out, or should be capable of being harmlessly absorbed within the body and naturally metabolized or excreted out.

Articulation paper, which uses a dye-impregnated material, has been used in dentistry for checking the 'bite' of a patient and has been established as biocompatible. The layer of dye-impregnated material consists of a micronized color pigment in an oil-wax emulsion covered with transculase bonding agent. Such a dye transfer system can also be used in the implant template herein. Advantages of such a material are that it has a high color storage capacity, but releases the color easily under pressure.

An exemplary dye paper is manufactured by Bausch GmbH, Cologne, Germany. An exemplary composition of such paper is as in Table 1:

TABLE 1

| Substance | CAS Number | Concentration (%) |
|---|---|---|
| Pigment Blue C.I. 27 | 25869-00-5 | 10 |
| CI Pigment red 170 | 2786-76-7 | 10 |
| White mineral oil | Pharmaceutical quality | 50 |
| Natural waxes | Cosmetic/pharmaceutical quality | 30 |

In other embodiments, the dye may be similar to the dyes in the pens known in the art to outline the implant template in other types of surgery.

Sterile surgical skin markers for medical purposes are offered by several manufacturers, such as: Viscot (e.g., www.viscot.com/1422SRL9-100), and Tondaus.

Sterile ink has been used for tattooing, and may find application in the technology herein, to the extent that it does not matter if the ink remains in situ at the site of surgery. There are several manufacturers of such substances: for example, Body Supply: www.bodysupply.com/colori-per-tatuaggio.html; and www.killerinktattoo.nl/tattoo-inkt/. Some inks for tattooing are supplied in cups that can be sterilized by ethylene oxide and are described at: electrum-supply.com/sterile-single-packs-of-16-precision-ink-cup-3-x-3-sheets/

The implant template is a sterile template because it will be used in a sterile area. An embodiment of the invention is a single use sterile dye template that clips to an existing titanium reusable template.

Given that a template is sterilized prior to re-use, any sterilization process that can wash off the dye militates in favor of either dyes that can survive that process, or embodiments of the implant in which a fresh coating of dye or dye-impregnated material can be introduced after sterilization.

EXEMPLARY IMPLEMENTATIONS

This technology is straightforward to implement and can be applied across a range of implant products with little difficulty. It has application to any product that requires a portion of bone to be drilled away in connection with installation. The technology therefore offers distinct advantages over products that are not so equipped.

The technology can be applied to devices such as deep brain stimulators and auditory brain stem implants.

Figure 3A:
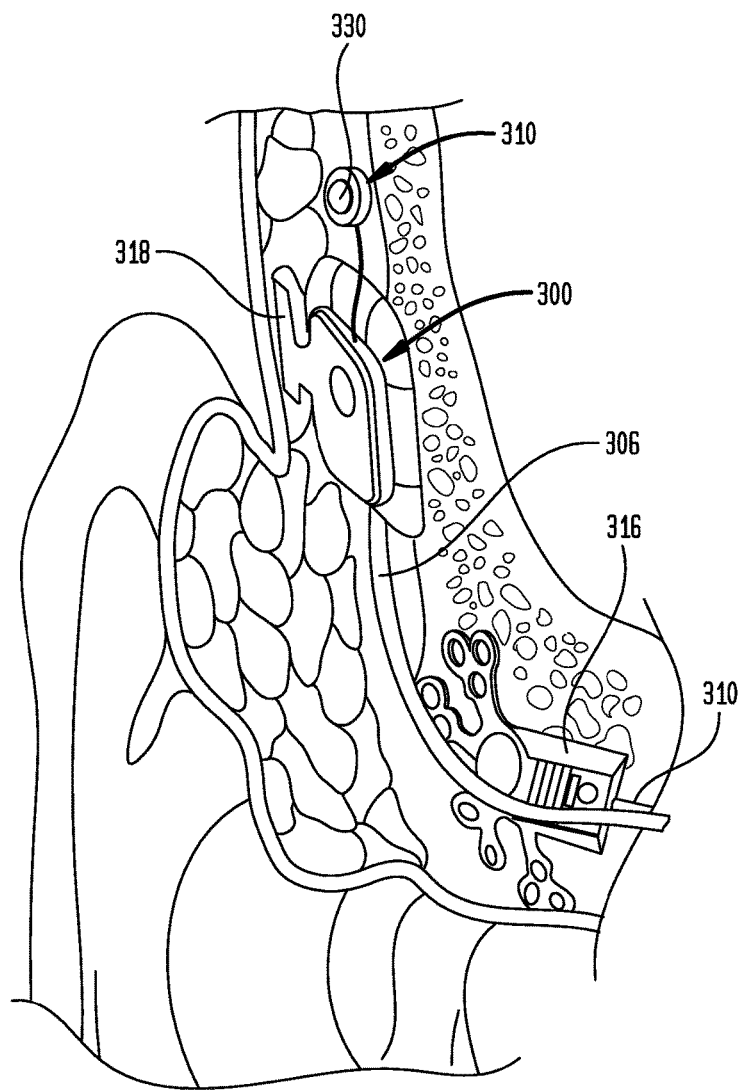
FIGS. 3A and 3B show schematics of various implantation environments.
Figure 3B:
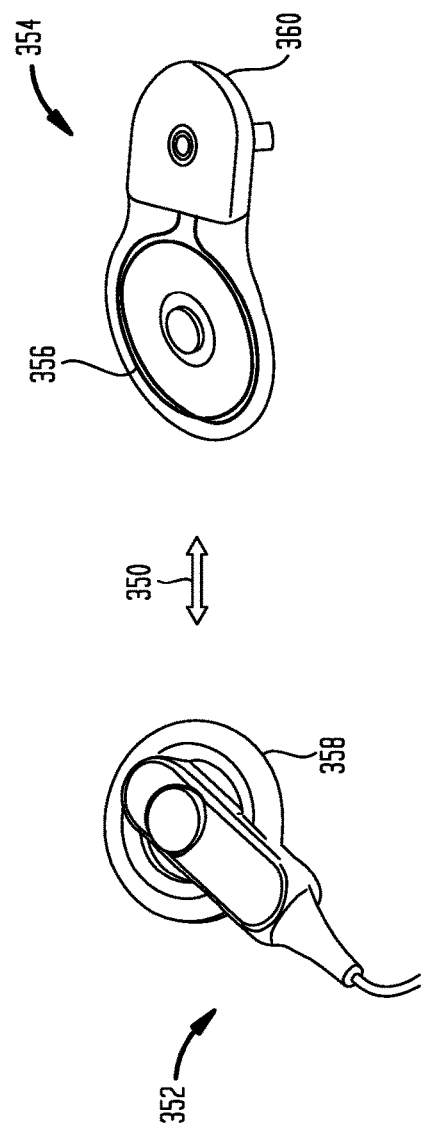

The technology can be applied to a surgically implanted microphone and/or an implant package for an active transcutaneous bone conduction device, as illustrated in FIGS. 3A and 3B, respectively.

In FIG. 3A, a biocompatible implant housing 300 is located subcutaneously on a patient's skull. The implant housing 300 includes a signal receiver 318 (e.g., comprising a coil element) and may include an integrated microphone or an separate implantable microphone 310 that is interconnected to the housing 300 via an electrical connector. In either case, microphone 310 will include a diaphragm 330 that is positioned to receive acoustic signals through overlying tissue. Typically, the signal processor within the implant housing 100 is electrically interconnected via wire 106 to a transducer (not shown). A positioning system 110 is connected to a bone anchor 116 mounted within the patient's mastoid process (e.g., via a hole drilled through the skull). During normal operation, acoustic signals are received subcutaneously at the microphone 310, which generates signals for receipt by the housing 300. Upon receipt of the signals, a signal processor within the implant housing 300 processes the signals to provide a processed audio drive signal via wire 306 to the transducer. Positioning of the microphone, in a bone recess, can be accomplished with the technology described herein.

In FIG. 3B, part of a transcutaneous bone conduction device is shown. External component 352 comprises an external coil 358 and operates in conjunction with an implantable component 354. The implantable component 354 comprises an implantable coil 356 that is embedded within an actuator assembly 360, and can be positioned using the technology described herein.

In particular, the technology can readily be used in otology in connection with affixing implantable audio prosthetic devices, such as cochlear implants as well as middle ear implants, bone conduction implants, direct acoustic cochlear stimulators, and vestibular stimulators.

The technology herein can also be applied to surgical templates used for active transcutaneous bone conduction device. Exemplary such devices are provided by Cochlear Limited. Other such devices include the fixation system in the Codacs™ series of products, or tools for drilling the bone bed for an active transcutaneous bone conduction device.

An active transcutaneous bone conduction device works by vibration so the bone should not touch the surface of the implant. A screw is implanted in the bone. All vibrational energy coming from the implant should go via that screw into the head and not by any other contact points. The template for this type of implant is the same dimension as the implant, and has a flat surface. There is less to be gained from reduction of biofilm risk in this type implant. By contrast, the bigger risk is that unintended contact from a piece of bone can reduce the functionality and impair performance of the implant.

The approach herein can also be applied to implants that are affixed without a pedestal, such as the Nucleus Profile implant from Cochlear Limited.

The approach herein can also be applied to implants such as the CI24RE from Cochlear Limited, which is held in place by placing skin above it, without need for screws or glue. Instead, a round bone bed is drilled so that the implant will not move. As the implant receiver/stimulator is the same as for the Codacs™ implant, the dye template can be used in the same way: to first outline the shape to be drilled away, and then to check the depth and flatness of the bony well.

The implant template herein can be distributed in conjunction with a model of implant. It can be accompanied, in its packaging, by an Instructions For Use booklet (IFU) for the surgeon to review. The IFU contains instructions for how to use the implant template in conjunction with affixing the implant.

The implant template may also be distributed as part of a surgical kit, such as with the implant itself. In some embodiments, implant templates are sold in a set (such as all the templates that are required for a certain type of implant), as exemplified in FIG. 5. The different templates can also be ordered separately. The template can be used over and over again (i.e., on successive recipients) with the same type of implant or can be single use.

Preferably the implant template is sold separately, optionally accompanied by a selection of replacement dye material, because the implant template may be re-used with the same type of implant to which it is modeled. The IFU may contain instructions for re-sterilization of the implant template after use.

EXAMPLES

Example 1: Exemplary Template Set for a Codacs™ Implant System

An exemplary set of templates, of which some can be provided with a dye-transfer material on their respective distal surfaces, is shown in FIG. 5. Any of the templates can be provided in kit form.

Tools and templates are available for the implant body, the fixation system and the actuator. The tools and templates have been designed such that they can be used by a right handed or left handed surgeon. All surgical tools and templates are from stainless steel, are reusable, re-sterilisable and are delivered unsterile. The surgical tools will typically pre-cleaned prior to packaging to ensure that they have undergone a degreasing process. They must also be sterilised by the clinic before use.

The BTE template 502 (see FIG. 5) is used to ensure that the implant and the fixation system are positioned with sufficient space for an ear level sound processor.

The implant template 504 (see FIG. 5) is used to check the shape of the well excavation and the position of the receiver/stimulator assembly 141 of FIG. 1D.

The bone recess template 506 (see FIG. 5) is used to mark the well on the skull and to measure the depth of the well after drilling.

The array exit marking template 508 (see FIG. 5) is used to check the size of the well excavation, select the final position of the implant by rotating the tool in the well, and mark the exit position and channel width for the cable that connects to the Codacs™ actuator.

A fixation system template 510 (see FIG. 5) has the same dimensions as the real fixation system. It only represents the ball joint part, without the ball joint itself and without the clamping mechanism.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the scope of the appended claims.

What is claimed:

1. A method of improving goodness of fit of an implant to a recipient's bone, the method comprising:
    placing a dye-impregnated surface of an implant template in contact with the bone so that the dye colors the bone at points that are raised above their surroundings;
    drilling the colored areas in order to ensure that the surface to which the bone implant is affixed is smooth and has the correct width and depth so that the implant fits well in the drilled out area and will not move after implantation.

2. A method for minimizing biofilm formation between an implant and a bone, the method comprising:
    placing a dye-impregnated surface of an implant template in contact with the bone so that the dye colors the bone at points that are raised above their surroundings;
    drilling the colored areas in order to ensure that the surface of the bone to which the implant is affixed is smooth and thereby does not result in pockets between the surface of the bone and a surface of the implant that is to be attached to the bone.

3. A method for placing an implant, the method comprising:
    placing a distal surface of an implant template in contact with a bone, wherein the template has the same size and shape as the implant;
    delineating an area of the bone at which to affix the implant;
    drilling out the bone within the delineated area in order to accommodate the implant;
    inserting the template into the drilled out area so that a layer of dye impregnated material on the distal surface of the template is in contact with a proximal surface of the bone and edges of the drilled out area;
    drilling further regions of the drilled out area that are colored by the dye;
    repeating the inserting and drilling further regions until the drilled out area is uniformly coated with dye upon contact with the template; and
    affixing the implant to the drilled out area.

4. The method of claim 3, wherein the delineating includes using the dye impregnated template as a stamp to mark the area to be drilled out on the bone, without needing to draw a line around the template.

5. The method of claim 3, wherein the placing the distal surface of the template in contact with the bone comprises contacting the layer of dye-impregnated material on the distal surface of the template with the bone, and the delineating an area comprises identifying the area of bone that has been colored by the dye.

6. The method of claim 3, wherein the bone is selected from:
    skull, hip, jaw, and femur.

7. The method of claim 3, wherein the dye is a sterile biocompatible material selected from:
    surgical skin markers, tattoo ink, and micronized color pigment in oil-wax emulsion.

8. The method of claim 3, wherein the dye-impregnated material is a micro fleece paper with high color storage capacity.

9. The method of claim 3, wherein the implant is an implantable hearing prosthesis.

10. The method of claim 9, wherein the implantable hearing prosthesis is selected from: a cochlea implant, a middle ear implant, a bone conduction implant and a direct acoustic cochlear implant.

11. The method of claim 3, wherein the material is a sponge, a polymer, or a cellulose pad.

12. The method of claim 3, wherein the dye is biocompatible.

13. The method of claim 3, wherein the template is made of titanium.

14. The method of claim 3, wherein the repeating takes place from 1-5 times.

15. The method of claim 3 wherein the template has proximal and distal surfaces, and wherein the distal surface is covered in a dye-impregnated material, and wherein the proximal surface has an attachment member affixed to it.

16. The method of claim 15, wherein the attachment member is held by a surgeon when placing the template in contact with the bone.

17. A surgical tool, comprising:
    a surgical template configured to fit an implant to a recipient's bone, wherein the surgical template comprises a rigid first member having proximal and distal surfaces, and wherein the distal surface is configured to be covered in a dye-impregnated material, and wherein the proximal surface has an attachment member affixed to it,
    wherein the first member has the same size and shape as the implant.

18. The surgical tool of claim 17, wherein the first member is planar.

19. The surgical tool of claim 17, wherein the surgical template is made of titanium.

20. The surgical tool of claim 17, wherein the dye-impregnated material is a sponge, a polymer, or a cellulose pad.

21. The surgical tool of claim 17, wherein the dye-impregnated material is a micro fleece paper with high color storage capacity.

22. The surgical tool of claim 17, wherein the dye is biocompatible.

23. The surgical tool of claim 17, wherein the dye is a sterile biocompatible material selected from: surgical skin markers, tattoo ink, and micronized color pigment in oil-wax emulsion.

24. A surgical kit comprising:
   a dye; and
   a surgical template comprising a first member having distal and proximal surfaces, and wherein the distal surface is covered in an absorbent material, and wherein the proximal surface has an attachment member affixed to it,
   wherein the first member has the same size and shape as a bone implant.

25. The surgical kit of claim 24, wherein the first member is planar.

26. The surgical kit of claim 24, further comprising the bone implant.

27. The surgical kit of claim 24, wherein the absorbent material is a sponge, a polymer, or a cellulose pad.

28. The surgical kit of claim 24, wherein the absorbent material is a micro fleece paper with high color storage capacity.

29. The surgical kit of claim 24, wherein the dye is biocompatible.

30. The surgical kit of claim 24, wherein the dye is a sterile biocompatible material selected from: surgical skin markers, tattoo ink, and micronized color pigment in oil-wax emulsion.

\* \* \* \* \*